United States Patent [19]

Jones et al.

[11] 4,042,978

[45] * Aug. 23, 1977

[54] PROSTHETICS

[75] Inventors: Michael Edward Benet Jones; Eileen Jones; Joseph Franciszek Jaworzyn, all of Runcorn, England

[73] Assignee: Imperial Chemical Industries Limited, London, England

[*] Notice: The portion of the term of this patent subsequent to Sept. 30, 1992, has been disclaimed.

[21] Appl. No.: 585,868

[22] Filed: June 11, 1975

Related U.S. Application Data

[62] Division of Ser. No. 368,199, June 8, 1973, Pat. No. 3,908,201.

[30] Foreign Application Priority Data

June 30, 1972 United Kingdom ............... 30766/72

[51] Int. Cl.$^2$ ........................... A61F 1/24; A61F 1/00; C08G 63/18; C08L 63/10
[52] U.S. Cl. ................................. 3/1; 3/1.4; 3/1.5; 128/334 R; 260/47 R; 260/47 C; 260/75 R; 260/77.5 R; 260/78 R; 260/836; 260/857 PG; 260/858; 260/860; 260/897 R; 260/901; 526/11.2
[58] Field of Search ............... 260/75 R, 89.5 A, 836, 260/860, 901; 3/1, 1.4, 1.5; 128/334 R; 526/11.2

[56] References Cited

U.S. PATENT DOCUMENTS

| 2,589,688 | 3/1952 | Flory et al. | 260/75 R |
|---|---|---|---|
| 3,320,972 | 5/1967 | High et al. | 3/1.5 X |
| 3,463,158 | 8/1969 | Schmitt et al. | 3/1 X |
| 3,563,925 | 2/1971 | Kliment et al. | 3/1 X |
| 3,588,920 | 6/1971 | Weslowski | 3/1 |
| 3,607,848 | 9/1971 | Stoy et al. | 3/1 X |
| 3,656,185 | 4/1972 | Carpentier | 3/1 |
| 3,681,786 | 8/1972 | Lynch | 3/1 |
| 3,688,317 | 9/1972 | Kurtz | 3/1 |
| 3,766,567 | 10/1973 | Kahn et al. | 3/1 |
| 3,886,125 | 5/1975 | Chromecek | 260/89.5 A X |

OTHER PUBLICATIONS

Owens et al., *Journal of Applied Polymer Science*, vol. 13, pp. 1741-1747 (1969).

*Primary Examiner*—Howard E. Schain
*Assistant Examiner*—W. C. Danison, Jr.
*Attorney, Agent, or Firm*—Cushman, Darby & Cushman

[57] ABSTRACT

A prosthetic device having at least part of the surface thereof made of a material having a surface energy, as hereinbefore defined, in the range 50 erg cm$^{-2}$ to 100 erg cm$^{-2}$, for example, made of a plastics material which is a copolymer comprising repeat units having the structure —CH$_2$—CH$_2$—O— and other units capable of stabilizing the copolymer in water, the copolymer comprising at least 10% by weight of units having the structure —CH$_2$—CH$_2$—O— and no more than 95% by weight of said units.

17 Claims, No Drawings

PROSTHETICS

This is a division of application Ser. No. 368,199 filed June 8, 1973, now U.S. Pat. No. 3,908,201.

This invention relates to prosthetic devices and in particular to prosthetic devices which are to be used internally in the body.

Prosthetic devices made, for example, of platics materials have been used internally in the body, and in particular in the human body. Plastics materials which have been proposed for use in this application include, for example, polytetrafluroethylene, polyethylene, poly(ethylene terephthalate), and nylon, e.g. poly(hexamethylene adipamide). Devices made of such materials may function satisfactorily, even over a prolonged period of time, provided the devices are not subjected to a load.

However, prosthetic devices made, for example, from such plastics materials have sufferred from the disadvantage that when used internally in the body the collagenous body tissues, that is the main load-bearing tissues, which form around and in contact with the prosthetic device in the body form at most only a weak bond at the interface with the surface of the device with the result that, when the device is subjected to a load, failure may occur at the interface between the prosthetic device and collagenous body tissue.

This susceptibility to failure is a limiting factor in the long term use of internal prosthetic devices, and in particular of prosthetic devices made of plastics materials, and may be particularly serious where the prosthetic device in the body carries a fluid, e.g. bile or urine, as failure may result in leakage of the fluid and infection in the body.

In order to attempt to overcome this disadvantage, at least to some extent, and in particular to provide prosthetic devices to which collagenous body tissues will bond more strongly than has been the case with the materials which have been proposed for use hiterto, we have determined the surface energies of a number of collagenous body tissues, both human and animal, and the surface energies of a number of platics materials which have been proposed for use hitherto in prosthetic devices.

We have found that the surface energies of many collagenous body tissues when fresh, that is, shortly after removal of the tissue from the body, are in general at least 65 erg. cm$^{-2}$, generally are the range 70 to 75 erg cm$^{-2}$, whereas the surface energies of the plastics materials which have been used hitherto to make prosthetic devices are as low as 14 erg cm$^{-2}$, and in general are no higher than 45 erg cm$^{-2}$.

For example, we have measured the surface energies of a number of collagenous body tissues and have found that the surfce energy of, for example, rectus sheath from the human body is 72.1 erg cm$^{-2}$, that of the pericardium of a dog is between 66.7 and 70.6 erg cm$^{-2}$, that of the pleural membrane of a dog is 72.2 erg cm$^{-2}$, that of the peritoneum of a human being is in the range 70.4 to 71.4 erg cm$^{-2}$, and that of scar tissue from a human being is 73.5 erg cm$^{31\ 2}$. On the other hand, the surface energies of plastics materials which have been proposed for use in prosthetic devices are generally considerably less than the aformentioned tissue surface energies, for example, polyethylene (low density) 33.1 erg cm$^{-2}$, poly(tetrafluoroethylene) 14.0 erg cm$^{-2}$, nylon 6,6 43.2 erg cm$^{-2}$, and poly(ethylene terephthalate) 41.3 erg cm$^{-2}$.

We have found that as the surface energy of the plastics material from which the prosthetic device is made increases and approaches the surface energy of the collagenous body tissue with which it is to be contacted than the strength of the bond formed at the interface between the collagenous body tissue and the prosthetic device increases.

As stated hereinbefore the surface energies of plastics materials used hitherto to make prosthetic devices are generally considerably less than the surface energies of the collagenous body tissues. Prosthetic devices may be made from other materials, e.g. metals. In general metals have surface energies considerably higher than the surface energies of the collagenous body tissues and prosthetic devices made from metals suffer from the same disadvantages as prosthetic devices made from plastics materials.

We have also found that the strength of the bond formed at the interface between the collagenous body tissue and the prosthetic device is stronger the more nearly does the surface energy of the material from which the prosthetic device is made approach that of the collagenous body tissue.

According to the present invention there is provided a prosthetic device having at least part of the surface thereof made of a material having a surface energy, as hereinafter defined, in the range 50 erg cm$^{-2}$ to 100 erg cm$^{-2}$.

By surface energy we mean the surface energy as measured by the method described in Journal of Colloid and Interfacial Science, Volume 31(2), pages 211 to 227, (1969).

By prosthetic device we means an article having a shape suitable for use in the human or animal body and in particular for use in place of a part of the human or animal body. It may have a shape suitable for use as, for example, a cosmetic implant, e.g. in the nose; a duct, e.g. a bile or urinary duct; an arterial graft; an anchor point, e.g. for a heart valve; or a net, e.g. a net for a hernia repair.

At least that part of the surface of the device which, when the device is implanted in the body, will be in contact with the collagenous tissue should be made of the aforementioned material and the material should possess the aforementioned surface energy when the device is implanted in the body. Suitably the whole of the surface of the device may be made of the aforementioned material.

The prosthetic device may be made from any material provided at least part of the surface of the device is made of a material which satisfies the surface energy requirements herenbefore described, and provided the material or materials from which the device is made are non-toxic and are fabricatable into the desired shape of the prosthetic device and provided the device is sterilisable and is biostable, that is provided the device does not degrade in the body environment. For example, the device may, if desired, be made in part of a material hich does not satisfy the aforementioned surface energy requirements provided at least part of the device is made of a material satisfying the aforementioned surface energy requirements. Thus, at least part of the surface of the device may carry a coating or layer of a material satisfying the aforementioned surface energy requirements. Suitably, substantially the whole of the surface of the device is made from a material satisfying the surface energy requirments hereinbefore described. If desired, substantially the whole of the device may be made from a material satisfying the surface energy requirements.

The prosthetic device is suitably made of a plastics material, e.g. a thermoplastic.

The nearer the surface energy of the material from which the prosthetic device or at least part of the surface thereof is made approaches the surface energy of the collagenous body tissue with which it is to be contacted, the stronger is the bond at the interfere between the collagenous body tissue and the surface of the prosthetic device, and for this reason it is preferred, as many collagenous body tissues have surface energies in the range 70 to 75 erg cm$^{-2}$, that the surface energy of the material from which the prosthetic device or at least part of the surface thereof is made be in the range 60 erg cm$^{-2}$ to 85 erg cm$^{-2}$, and more preferably in the range 65 erg cm$^{-2}$ to 80 erg cm$^{-2}$.

A suitable platics material from which a prosthetic device, or at least part of the surface thereof, may be made comprises at least one polymeric material comprising repeat units having the structure —CH$_2$—CH$_2$—O— and at least one other component capable of stabilising the plastics material in water.

As a polymeric material consisting substantially entirely of repeat units having the structure —CH$_2$—CH$_2$—O—, that is, the polyethylene oxide or poly(ethylene glycol) is water soluble, it is essential that the plastics material include at least one other compound capable of stabilising the plastics material in water.

By water stability we means that the polymeric material should be stable in water at least to the extent that a film of the material 0.5 mm thick which has been immersed in water at 37° C for 24 hours should not break when flexed through 180°.

For example, the plastics material may comprise a blend of at least one polymeric material comprising repeat units having the structure —CH$_2$—CH$_2$—O and at least one other polymeric material, the other polymeric material, hereinafter referred to as the stabilising polymeric material, conferring on the plastics material the required water stability. The polymeric material comprising —CH$_2$—CH$_2$—O— units may, for example, be poly(ethylene oxide) or poly(ethylene glycol) and the stabilising polymer material may be formed by polymerisation of, for example, at least one ethylenically unsaturated monomer. Thus, the plastics material may be formed from a blend of polymeric material comprising repeat units having the structure —CH$_2$—CH$_2$—O— and at least one polymerisable material, e.g. a polymerisable ethylenicaly unsaturated monomer, by polymerising the polymerisable material in the blend. Suitable polymerisable monomers include vinyl monomers, e.g. alkyl acrylates and alkyl methacrylates, e.g. methyl acrylate, ethyl acrylate, propyl acrylate, butyl acrylate, methyl methacrylate, ethyl methacrylate, propyl methacrylate and butyl methacrylate, styrene, vinyl toluene and polymerisable monomers containing at least two polymerisable ethylenically unsaturated groups, e.g. divinyl benzene and ethylene glycol diemthacrylate.

The stabilising polymeric material should confer on the plastics material the required water stability and is desirably present in the plastics material in a proportion in the range 10% to 50% by weight of polymeric material comprising repeat units having the structure —CH$_2$—CH$_2$—O—.

A suitable plastics material processing the required water stability and which may be used to form the prosthetic device, or at least a part of the surface thereof, is a copolymer comprising repeat units having the structure —CH$_2$—CH$_2$—O— and other units capable of stabilising the copolymer in water, the copolymer comprising at least 10% by weight of units having the structure CH$_2$—CH$_2$—O— and no more than 95% by weight of said units.

The copolymer containing —CH$_2$—CH$_2$—O— repeat units should, of course, also have a molecular weight sufficiently high that the material is solid, and it is preferred, although not essential, that the molecular weight of the copolymer is sufficiently high that the reduced viscosity of a 1% weight/volume solution of the material in o-chlorophenol at 25° C is at least 0.4 dl.g$^{-1}$, preferably at least 0.6 dl.g$^{-1}$. The upper limit of molecular weight is determined by the degradation which may take place during production of the copolymer if a very high molecular weight copolymer is made. A suitable upper limit of molecular weight is that at which the reduced viscosity of the copolymer is not greater than 2.0 dl.g$^{-1}$, measured as hereinbefore described. The molecular weight of the copolymer which is required will depend on the nature of the stabilising units in the copolymer.

In order that the surface energy of the plastics material should more closely approach that of collagenous body tissue, and should thus form a stronger bond with collangenous body tissue, it is preferred that the copolymer comprise between 30 and 80% by weight of units having the structure —CH$_2$—CH$_2$—O—, and more preferably should comprise between 50 and 80% by weight of units having the aforementioned structure.

The units in the copolymer which are capable of stabilising the material in water may be, for example, ester-containing units, urethane-containing units, or amide-containing units.

For example, the ester containing units may have the structure:

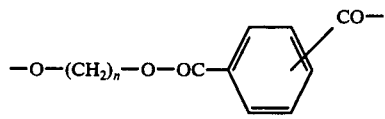

where $n$ is a whole number in the range 2 to 8, and in which the carbonyl groups are attached meta or para to the aromatic ring. The aromatic ring may carry substituent groups other than hydrogen, for example, chloro, nitro or alkoxy, e.g. methoxy groups, provided these groups do not interfere with the formation of the copolymer. $n$ is suitably a whole number of 2, 3 or 4. Preferred units in the copolymer which are capable of stabilising the material in water are ethylene terephthalate or ethylene isophthalate units, or mixtures thereof. If desired, the ester-containing units may be derived from a binuclear aromatic diacid, e.g. an acid of the structure:

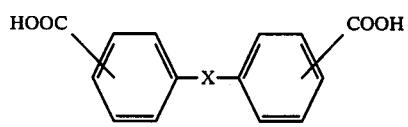

where X is a divalent group, e.g. —O—, —SO$_2$, —CH$_2$—, and one or other or both of the carboxylic groups are in a position meta or para to the group —X—.

It will be noted that where the stabilising units in the copolymer are ester containing units having the structure:

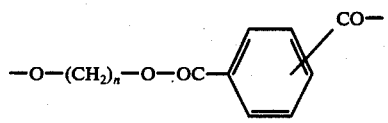

in which $n$ is 2 these ester units contain, inter alia, $-CH_2-CH_2-O-$ units. These latter $-CH_2-CH_2-O-$ units are to be considered as forming part of the ester containing units and where we refer to a copolymer containing from 10 to 95% by weight of units having the structure $-CH_2-CH_2-O-$ we mean a copolymer containing 10 to 95% by weight of such units excluding any $-CH_2-CH_2-O-$ units which form part of a stabilising unit such as an ester containing unit.

The $CH_2-CH_2-O-$ units in the copolymer may be in the form of blocks. In this case the length of the blocks has a bearing on the water stability of the copolymer. We find that where there are up to 50% by weight of $-CH_2-CH_2-O-$ units in the copolymer the water stability is unaffected by the block length at least up to a block length of 6000 molecular weight. Between 50 and 70% by weight $-CH_2-CH_2-O-$ units in the copolymer it is preferred, on account of the high water stability of the materials, that the block length of the $-CH_2-CH_2-O-$ units be such that the blocks have a molecular weight in the range 500 to 5000. Similarly, with between 70 and 80% by weight of $-CH_2-CH_2-O-$ units in the copolymer the block length of the latter units is preferably such that the blocks have a molecular weight in the range 2000 to 5000.

The copolymers may be made by condensing poly(ethylene glycol), that is, a polymer having repeat units of the structure $-CH_2-CH_2-O-$, having the desired molecular weight, with an ester-generating compound, i.e. with a compound capable of producing in the polymeric material ester units which stabilise the copolymer in water. The condensation may be effected by technique well-known in the art of condensation polymer chemistry. Thus, for example, poly(ethylene glycol) may be condensed with a bis(hydroxy ethyl) ester of the diacid.

Alternatively, the poly(ethylene glycol) may be condensed with a mixture of the diacid, or dialkyl ester of the diacid, and glycol from which the ester which are derived, or with the polyester itself.

The condensation may be effected in the presence of a catalyst the nature of which will depend on the nature of the reaction taking place. Thus, where the ester-generating compound is a bis(hydroxy ethyl) ester of the diacid then catalysts for the condensation reaction include polymerisation catalysts e.g. $Sb_2O_2$ and $GeO_2$. Where the ester-generating compound is a mixture of a diacid and glycol then the condensation may be effected in the presence of an esterification catalyst, e.g. o-phosphoric acid, p-toluene sulphonic acid, or sodium alkoxide, and a polymerisation catalyst.

The condensation reaction may suitably be effected at a temperature in the range 180° to 300° C although care should be exercised to ensure that the temperature used is not so high that excessive degradation of the polymeric material occurs.

Prosthetic devices may be made from the plastics material by techniques well known in the art of polymer fabrication, for example, by casting from a solution of the plastics material, or by compression moulding, injection moulding or by extrusion of the plastics material, or by applying a coating of plastics material to at least part of the surface of a device, e.g. by applying to the surface of the device a solution of the plastics material and subsequently removing the solvent, e.g. by evaporation.

It is known, as described in Journal of Applied Polymer Science Volume 13, pages 1741-1747 (1969) that the surface energy ($\gamma s$) of a material may be considered to be made up of at least two components, a polar component ($\gamma s^h$) and a dispersion component ($\gamma s^d$) such that $\gamma s = \gamma s^h + \gamma s^d$. The surface energy components of the materials, e.g. plastics materials, which have been proposed for use hitherto in the production of prosthetic devices are generally such that $\gamma s^d$ is greater than $\gamma s^h$. We have found that for many collagenous body tissues the surface energy is made up of components in which $\gamma s^h$ is greater than $\gamma s^d$.

We believe that not only is a stronger bond formed between collagenous body tissue and a prosthetic device the more nearly do the surface energies of the collagenous tissue and the material from which at least part of the surface of the device is made approach each other, we also believe that, for a prosthetic device at least part of the surface of which is made of material having a given surface energy which surface energy is similar to or the same as that of the collagenous tissue a stronger bond is formed with collagenous tissue if the surface energy of the material is made up of components $\gamma s^h$ and $\gamma s^d$ in which $\gamma s^h$ is greater than $\gamma s^d$ than is the case where $\gamma s^d$ is greater than $\gamma s$.

In a further embodiment of our invention we provide a prosthetic device as hereinbefore described in which the surface energy ($\gamma s$) of the material of which at least part of the surface of the prosthetic device is made is in the range 50 erg cm$^{-2}$ to 100 erg cm$^{-2}$ and which comprises a surface energy component $\gamma s^h$ (as defined in the aforementioned Journal of Applied Polymer Science Volume 13, page 1741-1747, (1969)) which is greater than the surface energy component $\gamma s^d$ (as defined in the aforementioned Journal of Applied Polymer Science, Volume 13, page 1741-1747, (1969)).

We find that plastics materials from which the prosthetic device or at least part of the surface thereof may be made may have a surface energy made up of components $\gamma s^h$ and $\gamma s^d$ in which $\gamma s^h$ is greater than $\gamma s^d$ and have a surface energy in the range 50 erg cm$^{-2}$ to 100 erg cm$^{31\ 2}$ provided the plastics material consists essentially of the copolymer containing 65 to 75% by weight, and preferably about 70% by weight of units having the structure $-CH_2-CH_2-O-$, and 35 to 25% preferably about 30% by weight of other units, e.g. ethylene terephthalate units, capable of stabilising the copolymer in water, and provided also the $-CH_2-CH_2-O-$ units are present in blocks of length 600 to 6000 molecular weight, preferably 3800 to 4200 molecular weight, and more preferably in the region of 4000 molecular weight.

The invention is now illustrated by the following Examples in which all parts are expressed as parts by weight.

Contact angles and surface engergies ($\gamma s$) were measured by the method described in Journal of Colloid and Interfacial Science, Volume 31 (2), pages 211-227, (1969) and the values of $\gamma s^d$ and $\gamma s^h$ were calculated by the method described in Journal of Applied Polymer Science, Volume 13, pages 1741-1747, (1969).

The collagenous tissue to be studied was prepared in such a way that a flat surface suitable for contact angle measurements was obtained.

For example, the heart of a dog was exposed and an incision approximately ¾ inch long was made in the pericardium. A clean glass slide was inserted through the incision until an area of the glass slide measuring approximately 1 × ¾ inch was covered by the pericardium membrane. A cut was then made in the membrane around the periphery of the glass slide leaving a flat membrane on the surface of the slide.

The membrane on the slide was then washed repeatedly with saline solution at 30° C and then with distilled water. Thereafter, the tissue surface was exposed to a current of air at room temperature for 3 minutes and the tissue was then conditioned for 20 minutes in an atmosphere saturated with water vapour.

Contact angles were then determined on the tissue using water and methylene iodide as the liquids and the values of $\gamma s^h$, $\gamma s^d$ and $\gamma s$ were calculated from the contact angles of these two liquids using the method described in Journal of Applied Polymer Science Volume 13, pages 1741 to 1747, (1969).

In an alternative method a 1 cm. diameter disc of poly(ethylene terephthalate) was implanted subcutaneously in the back of a rat. After 1 month the disc and surrounding tissue were removed. The fibrous capsule surrounding the implanted disc was readily removed from the disc as there was little if any adhesion. After mounting on a glass slide the fibrous tissue surface which had been adjacent to the surface of the implanted disc was suitable for contact angle measurements and values of $\gamma s^h$, $\gamma s^d$ and $\gamma s$ were determined by following the procedure described above.

Using one or other of these methods the surface energies of a number of collagenous tissues were measured leading to the results hereinbefore described.

EXAMPLE 1

Preparation of a copolymer containing 20 wt. % ethylene oxy units 393 parts of bis($\beta$-hydroxylethyl) terephthalate were heated at 210° C under a stream of nitrogen until molten. 75 parts of poly(ethylene glycol) (average mol. wt. 4,000) were then added and the resultant mixture was stirred. After stirring for 15 minutes 0.18 part of antimony trioxide was added and stirring was continued for a further 15 minutes. The mixture was then transferred to a stirred, stainless steel polycondensation autoclave which had been pre-heated to 220° C. After stirring at this temperature for 10 minutes the temperature was raised to 280° C and after a further 30 minutes the autoclave was slowly evacuated. After 1½ hours at this temperature and under a vacuum of 0.4 mm of mercury stirring was stopped and the autoclave filled with nitrogen. The polymer was extruded from the autoclave and cooled and the rigid, opaque polymer was granulated. Yield: 315 parts of polymer of reduced viscosity 0.97 dl.g$^{-1}$ measured on a 1% weight/volume solution in o-chlorphenol at 25° C.

The surface of this material was determined on a flat, clean, dry surface of moulded polymer film 0.01 in. thick, $\gamma s = 64.3$ erg cm$^{-2}$, $\gamma s^h = 25.3$ erg cm$^{-2}$, $\gamma s^d = 39.0$ erg cm$^{-2}$. After immersion of the film in distilled water at 37° C for 3 days, followed by washing in fresh distilled water and conditioning for 20 minutes in an atmosphere saturated with water vapour the surface energy was as follows. $\gamma s = 50.2$ erg cm$^{-2}$, $\gamma s^h = 11.0$ erg cm$^{-2}$, $\gamma s^d = 39.2$ erg cm$^{-2}$.

EXAMPLE 2

Preparation of a copolymer containing 50 wt. % ethylene oxy units

262 Parts of bis($\beta$-hydroxylethyl)terephthalate and 200 parts poly(ethylene glycol) (average mol. wt. 4,000) were heated and admixed with 0.12 part antimony trioxide following the procedure described in Example 1 except that the polymer was extruded from the vessel after heating for 1¼ hours at 285° C under a vacuum of 0.4 mm of mercury.

The polymer was a pale brown, translucent, flexible material and had a reduced viscosity of 1.2 dl.g$^{-1}$ measured as described in Example 1. After immersion of a film of the polymer in distilled water for 3 days at 37° C the film was washed and conditioned following the procedure described in Example 1 and the surface energy was measured as follows. $\gamma s = 61.9$ erg cm$^{-2}$, $\gamma s^2$, $\gamma s^h = 30.0$ erg cm$^{-2}$, $\gamma s^d = 31.9$ erg cm$^{-2}$.

EXAMPLE 3

Preparation of a copolymer containing 70 wt. % ethylene oxy units

197 Parts bis($\beta$-hydroxyethyl)terephthalate, 350 parts poly(ethylene glycol) (average mol. wt. 4,000) were reacted in the presence of 0.09 part of antimony troxide following the procedure described in Example 1 to give 380 parts of a transparent rubbery polymer of reduced viscosity 1.42 dl.g$^{-1}$.

0.005 inch thick film of the polymer immersed in distilled water at 37° C for 3 days and washed and conditioned following the procedure described in Example 1 had the following surface energy. $\gamma s = 71.1$ erg cm$^{-2}$, $\gamma s^h = 42.9$ erg cm$^{-2}$, $\gamma s^d = 24.2$ erg cm$^{-2}$.

EXAMPLE 4

A copolymer containing 50% by weight of units derived from poly(ethylene glycol) of average molecular weight 600 and 50% by weight of units derived from poly(ethylene terephthalate) prepared as described in Example 2 was moulded into a 0.04 inch thick film and four 0.5 inch diameter discs were cut from the film. The discs were washed repeatedly with distilled water and sterilised by irradiating with ultraviolet radiation for 2 minutes.

Two of the discs were then implanted subcutaneously in the backs of each of the two rats. After 5 weeks the rats were sacrificed and the discs, together with the surrounding tissue, were removed and washed in 0.95% saline solution, touch dried with paper tissue, and dried in a dessicator over phosphorus peroxide at 20° C for 24 hours. Rectangular strips of dimensions 0.8 × 0.4 cm were then cut from the polymer/tissue combinations, the strips comprising a strip of polymer faced on both sides by tissue. Adhesive tape (sellotape) was then attached to the exposed tissue surfaces and to the jaws of an Instron Tensometer and the peel strength of the tissue-polymer bond was measured.

The average peel strength of the four samples tested was 12.4 g mm$^{-1}$.

By way of comparison, the procedure described above was repeated except that the discs of polymer were replaced by discs of poly(ethylene terephthalate)

having a surface energy of 41.3 erg cm$^{-2}$. In this case the bond strength between the discs of poly(ethylene terephthalate) and the tissue was too low to be measured. The surface energy of the tissue measured as hereinbefore described was 69.1 erg cm$^{-2}$ with $\gamma s^h$ being 34.2 erg cm$^{31\,2}$ and $\gamma s^d$ being 34.9 erg cm$^{-2}$.

EXAMPLE 5

The procedure described in Example 4 was repeated except that the discs were made of a copolymer prepared as described in Example 1.

The peel strength of the tissue-polymer bond was 7.8 g mm$^{-1}$.

EXAMPLE 6

Bis($\beta$-hydroxyethyl)isophthalate was prepared by mixing 120 parts of dimethylisophthalate, 97.5 parts of ethylene glycol and 0.1 part of manganese acetate and heating the mixture at 200° C under a slow stream of nitrogen. After heating for 1 hour the mixture was heated at 250° C for 10 minutes, 0.1 parts of phosphoric acid was added, and the mixture was cooled.

59.1 parts of the resultant polymer were mixed with 105 parts of poly(ethylene glycol) (average molecular weight 4,000) and 0.03 part of antimony trioxide. The mixture was heated at 200° C under a slow stream of nitrogen for 10 minutes and at a temperature of 250° C under a vacuum of 0.1 mm of mercury for 8 minutes. The vacuum was maintained and the temperature raised to 280° C over a period of 20 minutes and the mixture was maintained at this temperature for 45 minutes. After cooling the resultant product was a pale grey polymer having a reduced viscosity of 0.96 dl.g$^{-1}$.

The surface energy $\gamma s$ of a flat, clean, dry film measured following the procedure hereinbefore described was 57 erg cm$^{-2}$.

EXAMPLE 7

35 Parts of poly(ethylene oxide) powder (average molecular weight 4 $\times$ 10$^6$) were mixed with 11.7 parts of methyl methacrylate and 0.23 part of tertiary butyl perbenzoate. After mixing by hand for 10 minutes the resultant damp powder was placed in a twin-roll mill, the rolls of which have been preheated to 100° C. After mixing on the mill for 30 seconds the mixture was removed from the mill, cooled, and then compression moulded for 2 hours at 150° C under an applied pressure of 25 tons to produce a 0.01 inch thick film.

The surface energy of a clean, dry film was measured following the procedure hereinbefore described. $\gamma s = 70.5$ erg cm$^{-2}$, $\gamma s^h = 52.5$ erg cm$^{-2}$, $\gamma s^d = 17.9$ erg cm$^{-2}$.

EXAMPLE 8

The procedure of Example 7 was followed except that 35 parts of poly(ethylene oxide) powder (average molecular weight 6 $\times$ 10$^5$), 7 parts of methyl methacrylate and 0.2 part of tertiary butyl perbenzoate were used and the film which was produced had a thickness of 0.1 inch.

The surface energy of a clean, dry film was measured following the procedure hereinbefore described. $\gamma s = 65.2$ erg cm$^{-2}$, $\gamma s^h = 27.3$ erg cm$^{-2}$, $\gamma s^d = 37.9$ erg cm$^{-2}$.

The film was then immersed in distilled water at 37° C for 2 days, washed in fresh distilled water and conditioned following the procedure described in Example 1.

The surface energy of the resultant film was as follows. $\gamma s = 59.8$ erg cm$^{-2}$, $\gamma s^h = 28.6$ erg cm$^{-2}$, erg cm$^{-2}$.

EXAMPLE 9

The procedure of Example 7 was followed except that 35 parts of poly(ethylene oxide) (average molecular weight 4 $\times$ 10$^6$), 0.2 part of tertiary butyl perbenzoate, and, in place of the methyl methacrylate, 7.0 parts of ethylene glycol dimethyacrylate were used.

The surface energy of a clean, dry film was measured following the procedure hereinbefore described. $\gamma s = 66.3$ erg cm$^{-2}$, $\gamma s^h = 27.0$ erg cm$^{-2}$, $\gamma s^d = 39.3$ erg cm$^{-2}$.

After immersion in distilled water, washing and conditioning following the procedure described in Example 8 the surface energy of the film was as follows. $\gamma s = 59.7$ erg cm$^{-2}$, $\gamma s^h = 36.4$ erg cm$^{-2}$, $\gamma s^d = 23.3$ erg cm$^{-2}$.

EXAMPLE 10

Coplymers formed from bis($\beta$-hydroxyethyl)terephthalate and poly(ethylene glycol) and containing respectively 20%, 30% and 50% by weight of ethylene oxy units were prepared following the procedure described in Example 1. The copolymers were separately compression moulded into discs measuring 2.5 $\times$ 2.5 $\times$ 0.025 cm. The discs were washed repeatedly with distilled water, sterilised by irradiating with ultraviolet radiation for 24 hours and then subcutaneously implanted in sheep.

After 12 weeks the discs and surrounding tissue were removed from the sheep, treated following the procedure described in Example 4 and the peel strength of the bond between the tissue and each of the discs were measured.

The peel strengths were as follows.

| Weight % ethylene oxy units in copolymer | $\gamma s$ erg. cm$^{-2}$ | Peel Strength g mm$^{-1}$ |
|---|---|---|
| 20 | 50.2 | 5.1 |
| 30 | 56.3 | 7.8 |
| 40 | 61.9 | 21.0 |

By way of comparison when the above procedure was repeated using a disc of poly(ethylene terephthalate) the peel strength was zero.

EXAMPLE 11

0.02 inch thick poly(ethylene terephthalate) velour (Lusterite Products Limited ) was scoured by immersion in a 1% by weight aqueous solution of soda ash at 100° C for 15 minutes and was then washed repeatedly in distilled water. After drying, the velour was coated with a copolymer prepared following the procedure described in Example 2 by dipping the velour in a 20% by weight solution of the copolymer in chloroform, removing the velour, and allowing it to dry at room temperature. The coating procedure was repeated and the thus coated velour was sterilised by irradiating with ultra-violet radiation following the procedure described in Examples 4 and a 2 $\times$ 2 inch sample of the velour was implanted subcutaneously in a sheep.

After 10 weeks the velour was removed from the sheep and the velour was sectioned and examined by electron microscopy. Examination indicated marked growth of collagenous tissue into the velour, individual fibers of the velour having an intimate covering of tissue.

By way of comparison the above procedure was repeated except that the coating step was omitted. The uncoated velour, when removed from the sheep, showed much less ingrowth of tissue into the velour.

What we claim is:

1. A prosthetic device having a shape suitable for insertion into a human or animal body to replace a part thereof, said device having at least part of the surface thereof made of a plastic, water-soluble, non-toxic material having a surface energy in the range 50 erg cm$^{-2}$ to 100 erg cm$^{-2}$ whereby said device is capable of being bonded more strongly to collagenous body tissue than corresponding devices which do not have such a surface energy, said plastic material being a copolymer of poly(ethylene) glycol and bis($\beta$-hydroxy) isophthalate, the copolymer comprising at least 10% by weight of units having the structure $CH_2$—$CH_2$—O and no more than 95% by weight of said units and having a reduced viscosity measured on a 1% weight/volume solution in o-chlorphenol at 25° C in the range 0.4 dl.g$^{-1}$ to 2.0 dl.g$^{-1}$, wherein said polymeric material being stable in water to the extent that a film of material 0.5 mm. thick which has been immersed in water at 37° C for 24 hours does not break when flexed through 180°.

2. A prosthetic device as claimed in claim 1 said device being a bile or urinary duct.

3. A prosthetic device as claimed in claim 1, said device being a cosmetic implant.

4. A prosthetic device as claimed in claim 1, said device being an arterial graft.

5. A prosthetic device as claimed in claim 1, said device being an anchor point for a heart valve.

6. A prosthetic device as claimed in claim 1, said device being a net.

7. A prosthetic device as claimed in claim 1, wherein the copolymer contains polyethylene glycol in blocks of length 500 to 6000 molecular weight.

8. A prosthetic device having a shape suitable for insertion into a human or animal body to replace a part thereof, said device having at least part of the surface thereof made of a plastic, water-soluble, non-toxic material having a surface energy in the range 50 erg cm$^{-2}$ to 100 erg cm$^{-2}$ whereby said device is capable of being bonded more strongly to collagenous body tissue than corresponding devices which do not have such a surface energy, said plastics materal comprising a polymeric structure containing from 10 to 95% by weight of units of solid polyethylene oxide and from 90 to 5% of units of a polymerized methacrylate monomer wherein said plastics material being stable in water to the extent that a film of material 0.5 mm thick which has been immersed in water at 37+ C for 24 hours does not break when flexed through 180°.

9. A prosthetic device as claimed in claim 8, said device being a bile or urinary duct.

10. A prosthetic device as claimed in claim 8, said device being a cosmetic implant.

11. A prosthetic device as claimed in claim 8, said device being an arterial graft.

12. A prosthetic device as claimed in claim 8, said device being an anchor point for a heart valve.

13. A prosthetic device as claimed in claim 8, said device being a net.

14. A prosthetic device as claimed in claim 8, wherein the copolymer contains from 90 to 5% of units of polymerized methyl methacrylate.

15. A prosthetic device as claimed in claim 8, wherein the copolymer contains from 90 to 5% of units of polymerized glycol dimethacrylate.

16. A prosthetic device as claimed in claim 8, wherein the copolymer has a reduced viscosity measured on a 1% weight/volume solution in o-chlorphenol at 25° C in the range 0.4 dl.g$^{-1}$ to 2.0 dl.g$^{-1}$.

17. A prosthetic device as claimed in claim 8, wherein the copolymer contains between 30 and 80% by weight of units having the structure $CH_2$—$CH_2$—O.

* * * * *